United States Patent [19]

Takahashi et al.

[11] Patent Number: 5,221,339
[45] Date of Patent: Jun. 22, 1993

[54] HEAT-CONDUCTIVE SILICONE OIL COMPOUND

[75] Inventors: Takayuki Takahashi, Myogi; Satoshi Kuwata, Annaka, both of Japan

[73] Assignee: Shin-Etsu Chemical Co., Ltd., Chiyoda, Japan

[21] Appl. No.: 475,804

[22] Filed: Feb. 6, 1990

[30] Foreign Application Priority Data

Feb. 13, 1989 [JP] Japan .................................... 1-33307

[51] Int. Cl.$^5$ ................................................ C09K 5/00
[52] U.S. Cl. .............................. 106/287.13; 252/78.3; 252/74
[58] Field of Search .............. 252/74, 78.3, 572; 106/287.13

[56] References Cited

U.S. PATENT DOCUMENTS

| | | | |
|---|---|---|---|
| 2,831,008 | 4/1958 | Knopf et al. | 252/78.3 |
| 2,990,419 | 6/1961 | Nitzoche et al. | 252/78.3 |
| 3,885,984 | 5/1975 | Wright | 252/74 |

OTHER PUBLICATIONS

*Chemical Engineer's Handbook*, 5th ed., R. H. Perry et al., pp. 13-3, 1973.

*Primary Examiner*—Mark L. Bell
*Assistant Examiner*—C. M. Bonner
*Attorney, Agent, or Firm*—Wyatt, Gerber, Burke and Badie

[57] ABSTRACT

The silicone oil compound of the invention has a high thermal conductivity by virtue of compounding of a relatively large amount of a heat-conductivity improver such as zinc oxide, aluminum nitride and the like in a powdery form but still has an adequate and stable consistency suitable for application. This unique characteristic is obtained by the use of a specific silicone fluid as the base of the compound, which is a diorganopolysiloxane of which from 5 to 50% by moles of the silicon atoms at the molecular chain ends each have a hydroxy group bonded thereto.

5 Claims, No Drawings

HEAT-CONDUCTIVE SILICONE OIL COMPOUND

BACKGROUND OF THE INVENTION

The present invention relates to a novel heat-conductive silicone oil compound or, more particularly, to a heat conductive silicone oil compound which is free from the problem of an undue increase in the consistency even by increasing the amount of addition of the inorganic particulate material as an additive to impart the oil compound with high heat conductivity.

It is a conventional method that, when a silicone oil compound is to be imparted with a high heat conductivity, the silicone oil compound is admixed with an inorganic particulate material such as metal oxides, e.g., zinc oxide, aluminum oxide and the like, and inorganic nitrides, e.g., aluminum nitride, silion nitride and the like.

A problem in the heat-conductive silicone oil compound with admixture of the above mentioned inorganic particulate material as a heat conductivity improver is that, when the added amount of the heat-conductivity improver is increased with an object to obtain a higher and higher heat conductivity, the consistency of the oil compound is rapidly increased as the amount of the heat-conductivity improver is increased so that the oil compound can no longer be used in the applications as an oil compound. In other words, a silicone oil compound can be imparted with high heat conductivity only at the sacrifice of the usability in practical applications.

SUMMARY OF THE INVENTION

The present invention accordingly has an object to provide a silicone oil compound free from the above described problem in the conventional heat-conductive silicone oil compound or having high heat conductivity but still having good usability in applications as an oil compound.

Thus, the heat-conductive silicone oil compound of the invention comprises, as a blend: a) 100 parts by weight of an organopolysiloxane having a viscosity in the range from 10 to 100,000 centistokes at 25° C. and represented by the average unit formula $$R_aSiO_{(4-a)/2}, \qquad (I)$$

in which R is a group selected from the class consisting of unsubstituted or substituted monovalent hydrocarbon groups bonded to any silicon atoms and hydroxy group bonded t the silicon atom at the molecular chain end and the subscript a is a positive number in the range from 1.95 to 2.20, from 5 to 50% by moles of the terminal silicon atoms at the molecular chain ends each having a hydroxy group bonded thereto; and (b) from 150 to 900 parts by weight of an inorganic material selected from the class consisting of zinc oxide, aluminum oxide, aluminum nitride and silicon nitride in a powdery form.

DETAILED DESCRIPTION OF THE PREFERRED EMBODIMENTS

As is described above, the essential ingredients in the inventive heat-conductive silicone oil compound is the components (a) and (b), of which the most characteristic is the specific organopolysiloxane as the component (a). By virtue of the formulation with this unique component, the inventive silicone oil compound has a moderately low consistency with good usability even when the added amount of the inorganic particulate material as a heat-conductivity improver is greatly increased with an object to increase the heat conductivity of the compound.

The component (a) in the inventive heat-conductive silicone oil compound is an organopolysiloxane having a viscosity in the range from 10 to 100,000 centistokes at 25° C. and represented by the average unit formula $R_aSiO_{(4-a)2}$, in which R is a group selected from the class consisting of unsubstituted or substituted monovalent hydrocarbon groups and hydroxy group and the subscript a is a positive number in the range from 1.95 to 2.20. The unsubstituted or substituted monovalent hydrocarbon group denoted by R is exemplified by alkyl groups such as methyl, ethyl, propyl, butyl, hexyl, octyl, decyl, dodecyl and tetradecyl groups, alkenyl groups such as vinyl and allyl groups and aryl groups such as phenyl and tolyl groups as well as those substituted monovalent hydrocarbon groups obtained by replacing a part or all of the hydrogen atoms in the above named hydrocarbon groups with halogen atoms, cyano groups and the like such as chloromethyl, 3,3,3-trifluoropropyl and 2-cyanoethyl groups. It is essential in this organopolysiloxane that from 5 to 50% by moles of the silicon atoms at the molecular chain ends each have a hydroxy group bonded thereto but none of the silicon atoms other than the terminal ones has a hydroxy group bonded thereto.

The above mentioned hydroxy group-containing organopolysiloxane can of course be obtained, for example, by merely mixing a first organopolysiloxane of which all of the terminal silicon atoms each have a hydroxy group bonded thereto and a second organopolysiloxane terminated at each molecular chain end with a triorganosilyl group such as a trimethyl silyl group in a specified molar proportion. It is, however, preferable that a mixture of the above mentioned first and second organopolysiloxanes is subjected to a siloxane rearrangement reaction to equilibrium in the presence of an alkali metal hydroxide as a catalyst in a closed vessel followed by neutralization or removal of the alkaline catalyst and stripping of volatile matters under reduced pressure. By this means, the silicon-bonded hydroxy groups can be distributed evenly throughout all of the molecules.

Alternatively, the hydroxy group-containing organopolysiloxane suitable as the component (a) can be prepared by subjecting a mixture of a cyclic organopolysiloxane oligomer such as octamethyl cyclotetrasiloxane and a triorganosilyl-terminated diorganopolysiloxane to the siloxane rearragement reaction to equilibrium in a closed vessel in the presence of an alkali metal hydroxide as a catalyst and water followed by removal or neutralization of the alkaline catalyst and stripping of volatile matters under reduced pressure. It should be noted that the above mentioned stripping treatment of the reaction mixture must be performed at a temperature not exceeding 280° C. or, preferably, not exceeding 250° C. because, when the temperature is too high, the condensation reaction proceeds between the hydroxy groups at the molecular chain ends of the once formed hydroxy-terminated organopolysiloxane so that the content of the terminal hydroxy groups in the resultant organopolysiloxane may eventually be lower than the desired content.

The hydroxy terminated organopolysiloxane as the component (a) in the inventive silicone oil compound should have a viscosity in the range from 10 to 100,000 centistokes or, preferably, in the range from 100 to 10,000 centistokes at 25° C. When the viscosity of the organopolysiloxane is too low, no silicone oil compound having spreadability can be obtained by compounding the same with the inorganic particulate material in a fine powdery form as mentioned below. When the viscosity of the organopolysiloxane is too high, on the other hand, the silicone oil compound may have an extremely high consistency even by compounding with a relatively small amount of the fine powder of the inorganic material and a further amount of the powder can no longer be compounded consequently not to give a silicone oil compound of which the heat conductivity is sufficiently high.

The component (h) comprised in the inventive heat-conductive silicone oil compound is an inorganic material in a fine powdery form. Such an inorganic particulate material is well known in the prior art and used in conventional heat-conductive oil compounds including zinc oxide, aluminum, oxide, aluminum nitride and silicon nitride. The particles of the inorganic particulate material should have a particle diameter in the range from 0.1 to 20 μm. The configuration of the particles is not particularly limitative and can be a regular form or an irregular form.

It is optional according to need that the inventive heat-conductive silicone oil compound is further admixed with a known particulate filler such as carbon black, clay, bentonite and the like with an object to control the consistency or spreadability of the oil compound.

The heat conductive silicone oil compound of the invention can be prepared by blending the above described specific hydroxy-terminated organopolysiloxane fluid as the component (a) and the finely divided metal compound as the component (b) each in a specified and weighed amount by using a suitable blending machine. It is preferable that the thus obtained oil compound is imparted with improved uniformity and finished by further milling or kneading in a suitable milling machine such as three-roller mills, colloid mills, sand grinders, Gaulin homogenizers and the like, of which three-roller mills are particularly preferred.

In the following, the heat-conductive silicone oil compound of the present invention is described in more detail by way of examples, in which the term of "parts" always refers to "parts by weight" and the values of viscosity are all those obtained by the measurement at 25° C. The heat-conductive silicone oil comounds prepared in the following examples and comparative examples were evaluated for the consistency by the measurement of the penetration according to the method specified in JIS K 2220 and for the thermal conductivity determined by using a testing instrument of the hot-wire method (Model TC-1000, manufactured by Shinku Rico Co.).

EXAMPLE

In each of the 17 experiments, of which Experiments No. 1 to No. 10 were for the invention and No. 11 to No. 17 were for comparative purpose, a silicone oil compound was prepared by compounding 100 parts of one of the organopolysiloxanes specified below and a finely divided inorganic material, of which the kind and amount are shown in the table given below, in a planetary mixer for 30 minutes followed by three times of kneading on a three-roller mill. Each of the thus prepared silicone oil compounds was subjected to the measurement of the penetration as a measure of the consistency and thermal conductivity to give the results shown in the table.

ORGANOPOLYSILOXANES

Organopolysiloxane I: dimethyl polysiloxane having a viscosity of 520 centistokes, of which 20% by moles of the silicon atoms at the molecular chain ends each had a hydroxy group bonded thereto Organopolysiloxane II: dimethyl polysiloxane having a viscosity of 650 centistokes, of which 33% by moles of the silicon atoms at the molecular chain ends each had a hydroxy group bonded thereto Organopolysiloxane III: dimethyl polysiloxane having a viscosity of 490 centistokes, of which 5% by moles of the silicon atoms at the molecular chain ends each had a hydroxy group bonded thereto Organopolysiloxane IV: dimethyl polysiloxane having a viscosity of 105 centistokes, of which 13% by moles of the silicon atoms at the molecular chain ends each had a hydroxy group bonded thereto Organopolysiloxane V: dimethyl polysiloxane having a viscosity of 9,800 centistokes, of which 15% by moles of the silicon atoms at the molecular chain ends each had a hydroxy group bonded thereto Organopolysiloxane VI: dimethyl diphenyl polysiloxane having a viscosity of 1,100 centistokes, of which 5% by moles of the organic groups were phenyl groups and 10% by moles of the silicon atoms at the molecular chain ends each had a hydroxy group bonded thereto Organopolysiloxane VII: dimethyl diphenyl polysiloxane having a viscosity of 450 centistokes, of which 25% by moles of the organic groups were phenyl groups and 5% by moles of the silicon atoms at the molecular chain ends each had a hydroxy group bonded thereto Organopolysiloxane VIII: dimethyl decylmethyl poly siloxane having a viscosity of 450 centistokes, of which 25% by moles of the organic groups were decyl groups and 7% by moles of the silicon atoms at the molecular chain ends each had a hydroxy group bonded thereto Organopolysiloxane IX: dimethyl dodecylmethyl polysiloxane having a viscosity of 400 centistokes, of which 38% by moles of the organic groups were dodecyl groups and 5% by moles of the silicon atoms at the molecular chain ends each had a hydroxy group bonded thereto Organopolysiloxane X: dimethyl polysiloxane having a viscosity of 510 centistokes, of which 4% by moles of the silicon atoms at the molecular chain ends each had a hydroxy group bonded thereto Organopolysiloxane XI: dimethyl polysiloxane having a viscosity of 500 centistokes, of which 3% by moles of the silicon atoms at the molecular chain ends each had a hydroxy group bonded thereto Organopolysiloxane XII: dimethyl polysiloxane having a viscosity of 100 centistokes, of which 1.5% by moles of the silicon atoms at the molecular chain ends each had a hydroxy group bonded thereto Organopolysiloxane XIII: dimethyl polysiloxane having a viscosity of 1,000 centistokes, of which 2% by moles of the silicon atoms at the molecular chain ends each had a hydroxy group bonded thereto Organopolysiloxane XIV: dimethyl diphenyl polysiloxane having a viscosity of 400 centistokes, of which 25% by moles of the organic groups were phenyl groups and 1% by moles of the silicon atoms at the molecular chain ends each had a hydroxy group bonded thereto Organopolysiloxane XV: dimethyl decyl methyl polysiloxane having a viscosity of 400 centistokes, of which 25% by moles of the organic groups were decyl groups and 1% by moles of the silicon atoms at the molecular chain ends each had a hydroxy group bonded thereto Organopolysiloxane XVI: dimethyl polysiloxane having a viscosity of 650 centistokes, of which all of the silicon atoms at the molecular chain ends each had a hydroxy group bonded thereto

TABLE

| Experiment No. | Organopolysiloxane | Metal compound Kind | Metal compound Parts | Penetration, worked | Thermal conductivity, cal/cm.sec.°C. |
|---|---|---|---|---|---|
| 1 | I | ZnO | 300 | 350 | $2.0 \times 10^{-3}$ |
| 2 | II | AlN | 270 | 320 | $3.7 \times 10^{-3}$ |
| 3 | III | Al$_2$O$_3$ | 250 | 360 | $2.12 \times 10^{-3}$ |
| 4 | IV | ZnO | 400 | 320 | $2.50 \times 10^{-3}$ |
| 5 | V | ZnO | 233 | 330 | $1.85 \times 10^{-3}$ |
| 6 | VI | ZnO | 300 | 340 | $2.0 \times 10^{-3}$ |
| 7 | VII | Zl$_2$O$_3$ | 233 | 370 | $2.15 \times 10^{-3}$ |
| 8 | VII | AlN | 150 | 350 | $2.31 \times 10^{-3}$ |
| 9 | VIII | AlN | 250 | 360 | $3.30 \times 10^{-3}$ |
| 10 | IX | ZnO | 410 | 310 | $2.52 \times 10^{-3}$ |
| 11 | X | ZnO | 300 | 240 | $1.9 \times 10^{-3}$ |
| 12 | XI | Al$_2$O$_3$ | 250 | 190 | $2.0 \times 10^{-3}$ |
| 13 | XII | ZnO | 350 | 170 | $1.91 \times 10^{-3}$ |
| 14 | XIII | AlN | 233 | 135 | —* |
| 15 | XIV | Al$_2$O$_3$ | 240 | 230 | $2.0 \times 10^{-3}$ |
| 16 | XV | ZnO | 350 | 260 | $2.1 \times 10^{-3}$ |
| 17 | XVI | ZnO | 300 | 339 | $2.0 \times 10^{-3}$ |

*uniform coating layer not obtained

As is understood from the results shown in the table, each of the oil compounds, excepting that in Experiment No. 14, had a high thermal conductivity of at least $1.85 \times 10^{-3}$ cal/cm.sec.°C. as a result of compounding of an appropriate amount of the finely divided inorganic material. On the other hand, an adequate consistency could be obtained only in the oil compounds prepared in Experiments No. 1 to No. 10, which had a penetration as worked in the range from 310 to 370 to facilitate easy application to the heat-radiating board. The oil compounds prepared in Experiments No. 11 to 16 for comparative purpose had a small penetration of 135 to 260 to cause a difficulty in the application thereof to the heat-radiating board as a consequence of the use of an organopolysiloxane of which only 1 to 4% by moles of the terminal silicon atoms each had a hydroxy group bonded thereto. The oil compound in Experiment No. 17 was prepared by using an organopolysiloxane of which all of the terminal silicon atoms each had a hydroxy group bonded thereto. As a result, the consistency of the oil compound was subject to changes in the lapse of time with the value of penetration decreasing from 338 immediately after preparation to 205 after keeping for 10 days therefrom at about 20° C. to exhibit rubbery elasticity and to be not suitable for use as an oil compound.

What is claimed is:

1. A heat-conductive silicone oil compound which comprises, as a blend:
    (a) 100 parts by weight of an organopolysiloxane having a viscosity in the range from 10 to 100,000 centistokes at 25° C. and represented by the average unit formula $$R_a SiO_{(4-a)/2},$$

in which R is a group selected from the class consisting of unsubstituted or substituted monovalent hydrocarbon groups and hydroxy group bonded to the silicon atom at the molecular chain end and the subscript a is a positive number in the range from 1.95 to 2.20, from 5 to 50% by moles of the terminal silicon atoms at the molecular chain ends each having a hydroxy group bonded thereto; and
    (b) from 150 to 900 parts by weight of an inorganic material selected from the class consisting of zinc oxide, aluminum oxide, aluminum nitride and silicon nitride in a powdery form.

2. The heat-conductive silicone oil compound as claimed in claim 1 wherein the organopolysiloxane as the component (a) has a viscosity in the range from 100 to 10,000 centistokes at 25° C.

3. The heat-conductive silicone oil compound as claimed in claim 1 wherein the inorganic material in a powdery form as the component (b) has a particle diameter in the range from 0.1 to 20 μm.

4. The heat-conductive silicone oil compound as claimed in claim 1 wherein the monovalent hydrocarbon group in the component (a) denoted by R is an alkyl group or a phenyl group.

5. The heat conductive silicone oil compound as claimed in claim 1 wherein said component (a) is obtained by reacting a mixture of a first organopolysiloxane in which each of the terminal silicone atoms has a hydroxy group bonded thereto, with a second organopolysiloxane terminated at each end of the molecular chain with a triorganosilyl group, said reaction being conducted in a closed vessel under rearrangement conditions to equilibrium in the presence of an alkali metal catalyst, followed by neutralization of said catalyst and stripping any volatile matters produced during said reaction.

* * * * *